United States Patent
Kim et al.

(10) Patent No.: US 11,414,313 B2
(45) Date of Patent: Aug. 16, 2022

(54) WATER PURIFIER

(71) Applicant: LG ELECTRONICS INC., Seoul (KR)

(72) Inventors: Youngjin Kim, Seoul (KR); Beomchul Park, Seoul (KR); Jungmin Moon, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 481 days.

(21) Appl. No.: 16/469,493

(22) PCT Filed: Dec. 18, 2017

(86) PCT No.: PCT/KR2017/014971
§ 371 (c)(1),
(2) Date: Jun. 13, 2019

(87) PCT Pub. No.: WO2018/111056
PCT Pub. Date: Jun. 21, 2018

(65) Prior Publication Data
US 2020/0115212 A1 Apr. 16, 2020

(30) Foreign Application Priority Data
Dec. 16, 2016 (KR) .......................... 10-2016-0172957

(51) Int. Cl.
*A61L 2/10* (2006.01)
*B67D 1/08* (2006.01)
(Continued)

(52) U.S. Cl.
CPC .............. *B67D 1/0887* (2013.01); *A61L 2/10* (2013.01); *B67D 1/0888* (2013.01);
(Continued)

(58) Field of Classification Search
CPC .......... B67D 7/80; B67D 7/84; B67D 1/0888; B67D 1/0855; B67D 1/0884;
(Continued)

(56) References Cited

U.S. PATENT DOCUMENTS

| 128,570 A | * | 7/1872 | Wallace | B65D 25/48 |
| | | | | 222/567 |
| 230,167 A | * | 7/1880 | Bard | B65D 25/48 |
| | | | | 222/460 |

(Continued)

FOREIGN PATENT DOCUMENTS

| KR | 20-0327034 | 9/2003 |
| KR | 20-0393066 | 8/2005 |

(Continued)

OTHER PUBLICATIONS

International Search Report dated Apr. 5, 2018 issued in Application No. PCT/KR2017/014971.

*Primary Examiner* — Vishal Pancholi
*Assistant Examiner* — Michael J. Melaragno
(74) *Attorney, Agent, or Firm* — Ked & Associates, LLP

(57) ABSTRACT

A water purifier according to an embodiment of the present invention may include a housing accommodating components for generating cold water and/or hot water; and a water chute which protrudes from a front surface of the housing, in which the water chute includes a water cock through which cold water or hot water flows; and a light emitting element which is mounted on the water cock to emit ultraviolet rays, in which the water cock includes a water inflow part which extends in a transverse direction and has a water inflow passage formed therein; and a water outflow part which extends in a direction intersecting the water inflow part at an end of the water inflow part and has a water outflow passage formed therein, in which the light emitting element is disposed on the upper side of the water outflow (Continued)

part, and in which the water outflow passage includes a sloping part having a shape in which a cross-sectional diameter thereof gradually decreases toward the lower end thereof.

18 Claims, 9 Drawing Sheets

(51) Int. Cl.
 *B67D 1/12* (2006.01)
 *B01D 35/04* (2006.01)
 *B67D 1/07* (2006.01)
(52) U.S. Cl.
 CPC ......... *B67D 1/1277* (2013.01); *A61L 2202/11* (2013.01); *B01D 35/04* (2013.01); *B67D 2001/075* (2013.01)
(58) Field of Classification Search
 CPC .. B67D 1/0001; B67D 1/0005; B67D 1/0057; B67D 1/0058; B67D 1/008; B67D 1/0412; B67D 1/0431; B67D 1/045; B67D 1/0462; B67D 1/06; B67D 1/07; B67D 1/0801; B67D 1/0807; B67D 1/0835; B67D 1/0857; B67D 1/0862; B67D 1/0895; B67D 1/1202; B67D 2001/075; B67D 2201/0822; B67D 2001/1263; B67D 2210/0001; B67D 2210/0006; B67D 2210/00091; B67D 2210/00104; B67D 2210/00118; B67D 2210/00152; B67D 3/0012; B67D 3/0022; B67D 7/0216; B67D 7/82; A23L 2/54; A23L 2/60; A23L 33/105; A23L 33/135; A23L 33/40; A23L 7/104; A23L 7/197; A47J 31/02; A47J 31/40; A47J 31/44; A47J 31/4403; A47J 31/467
 USPC ............................ 222/146.1, 567; 210/748.1
 See application file for complete search history.

(56) References Cited

U.S. PATENT DOCUMENTS

| | | | | |
|---|---|---|---|---|
| 2,338,387 | A * | 1/1944 | Whitman | C12H 1/165 250/436 |
| 2,821,413 | A * | 1/1958 | Krapp | 285/18 |
| 4,792,059 | A * | 12/1988 | Kerner | B67D 3/00 222/129.1 |
| 5,131,571 | A * | 7/1992 | Nolley | B65D 47/06 222/1 |
| 5,855,795 | A * | 1/1999 | Chang | A61L 2/10 210/744 |
| 5,889,684 | A * | 3/1999 | Ben-David | B67D 1/0014 700/282 |
| 6,379,560 | B1 * | 4/2002 | Tilp | B01D 35/303 210/195.1 |
| 6,468,420 | B1 * | 10/2002 | Kunkel | C02F 1/008 210/192 |
| 7,790,022 | B2 * | 9/2010 | Underwood | C02F 9/005 210/91 |
| 8,710,459 | B1 * | 4/2014 | Davis, III | A61L 2/10 250/455.11 |
| 8,872,130 | B1 * | 10/2014 | Matthews | C02F 1/325 250/455.11 |
| 9,370,273 | B2 * | 6/2016 | Li | B67D 1/1218 |
| 10,556,808 | B2 * | 2/2020 | Gilbert | B01D 35/02 |
| 10,941,031 | B2 * | 3/2021 | Jung | B67D 1/0006 |
| 2004/0232175 | A1 * | 11/2004 | deCler | B67B 7/26 222/567 |
| 2011/0215037 | A1 * | 9/2011 | Cassassuce | B01D 35/14 210/95 |
| 2011/0315720 | A1 * | 12/2011 | Marshall | B65D 47/18 222/568 |
| 2012/0152985 | A1 * | 6/2012 | Gauthier | C25C 3/14 222/567 |
| 2012/0279926 | A1 * | 11/2012 | Riggers | C02F 1/32 210/748.1 |
| 2014/0131398 | A1 * | 5/2014 | Bardet | B65D 47/40 222/567 |
| 2014/0353222 | A1 * | 12/2014 | Sabin | B65D 47/06 210/94 |
| 2015/0007962 | A1 * | 1/2015 | Yoon | F28F 19/006 165/63 |
| 2015/0048116 | A1 * | 2/2015 | Orita | B67D 1/0009 222/146.1 |
| 2015/0114911 | A1 * | 4/2015 | Helmore | C02F 1/325 210/748.11 |
| 2015/0144653 | A1 * | 5/2015 | Kline | B67D 1/0027 222/1 |
| 2016/0002020 | A1 * | 1/2016 | Orita | B67D 3/0058 222/146.6 |
| 2016/0009537 | A1 * | 1/2016 | Orita | B67D 1/0009 222/144.5 |
| 2016/0009570 | A1 * | 1/2016 | Yu | C02F 1/325 210/748.1 |
| 2016/0016776 | A1 * | 1/2016 | Orita | B67D 1/0895 222/146.1 |
| 2016/0023880 | A1 * | 1/2016 | Forte | B67D 1/0895 134/18 |
| 2016/0046508 | A1 * | 2/2016 | Orita | B67D 1/07 222/146.1 |
| 2016/0168828 | A1 * | 6/2016 | Jeong | B67D 1/0014 137/10 |
| 2017/0050835 | A1 * | 2/2017 | Moon | H05B 6/108 |
| 2017/0050836 | A1 * | 2/2017 | Yoon | B67D 1/08 |
| 2017/0225972 | A1 * | 8/2017 | Sabin | C02F 1/32 |
| 2017/0320721 | A1 * | 11/2017 | Choi | B67D 1/0082 |
| 2017/0327388 | A1 * | 11/2017 | Kim | C02F 1/325 |
| 2017/0362071 | A1 * | 12/2017 | Showalter | B01F 15/00837 |
| 2018/0117208 | A1 * | 5/2018 | Graupner | A61L 2/10 |
| 2018/0170768 | A1 * | 6/2018 | Cho | A61L 2/10 |
| 2018/0194608 | A1 * | 7/2018 | Jeon | B67D 1/0888 |
| 2018/0215634 | A1 * | 8/2018 | Jung | A61L 2/10 |
| 2018/0229991 | A1 * | 8/2018 | Yu | C02F 1/687 |
| 2018/0271318 | A1 * | 9/2018 | Surface | A47J 31/404 |
| 2019/0016607 | A1 * | 1/2019 | Jeong | C02F 1/003 |
| 2019/0047877 | A1 * | 2/2019 | Geboers | E03C 1/0404 |
| 2019/0308865 | A1 * | 10/2019 | Yu | B67D 1/0857 |
| 2019/0308892 | A1 * | 10/2019 | Yu | B67D 1/07 |
| 2019/0382254 | A1 * | 12/2019 | Kim | C02F 1/008 |
| 2019/0382281 | A1 * | 12/2019 | Moon | B67D 1/0042 |
| 2019/0389712 | A1 * | 12/2019 | Kim | B67D 1/0878 |
| 2020/0114290 | A1 * | 4/2020 | Kim | B01D 35/16 |
| 2020/0156921 | A1 * | 5/2020 | Jung | B67D 1/0889 |
| 2020/0216331 | A1 * | 7/2020 | Jeon | B67D 1/0014 |
| 2021/0001366 | A1 * | 1/2021 | Yoon | B05B 15/68 |
| 2021/0001367 | A1 * | 1/2021 | Han | B67D 1/1236 |
| 2021/0001368 | A1 * | 1/2021 | Kim | B67D 1/0006 |
| 2021/0002117 | A1 * | 1/2021 | Park | B67D 1/0859 |
| 2021/0002119 | A1 * | 1/2021 | Kim | B05B 15/68 |
| 2021/0002121 | A1 * | 1/2021 | Jang | C02F 1/001 |
| 2021/0061638 | A1 * | 3/2021 | Park | B67D 1/08 |

FOREIGN PATENT DOCUMENTS

| | | |
|---|---|---|
| KR | 10-2007-0103282 | 10/2007 |
| KR | 10-2012-0037141 | 4/2012 |
| KR | 10-2014-0122138 | 10/2014 |

\* cited by examiner

WATER PURIFIER

CROSS-REFERENCE TO RELATED PATENT APPLICATIONS

This Applications is a U.S. National Stage Application under 35 U.S.C. § 371 of PCT Application No. PCT/KR2017/014971, filed Dec. 18, 2017, which claims priority to Korean Patent Application No. 10-2016-0172957, filed Dec. 16, 2016, whose entire disclosures are hereby incorporated by reference.

TECHNICAL FIELD

The present invention relates to a water purifier.

BACKGROUND ART

A water purifier can be defined as a device which filters harmful elements such as foreign substances or heavy metals contained in tap water.

A water purifying filter is used to purify the tap water flowing into the water purifier, and an ultraviolet sterilization method is used to sterilize the inside of a water cock from which water is discharged.

Korean Utility Model Registration No. 20-0393066 (Aug. 9, 2005) which is the related art discloses a structure for sterilizing water inside a water cock by mounting an LED which emits ultraviolet rays on an upper side of a water cock.

DISCLOSURE

Technical Problem

In a case of the related art, there are following problems.

Specifically, a part of light irradiated downward from the ultraviolet ray emitting LED mounted on an upper surface of the water cock may be exposed to the outside of the water purifier through the water cock, and the user may be injured by the exposed ultraviolet rays.

The present invention is proposed to solve the above problems.

Technical Solution

In order to achieve the above objective, according to an embodiment of the present invention, there is provided a water purifier which may include a housing accommodating components for generating cold water and/or hot water; and a water chute which protrudes from a front surface of the housing, in which the water chute includes a water cock through which cold water or hot water flows; and a light emitting element which is mounted on the water cock to emit ultraviolet rays, in which the water cock includes a water inflow part which extends in a transverse direction and has a water inflow passage formed therein; and a water outflow part which extends in a direction intersecting the water inflow part at an end of the water inflow part and has a water outflow passage formed therein, in which the light emitting element is disposed on the upper side of the water outflow part, and in which the water outflow passage includes a sloping part having a shape in which a cross-sectional diameter thereof gradually decreases toward the lower end thereof.

Advantageous Effect

According to the water purifier according to the embodiment of the present invention configured as described above, there is an advantage that the ultraviolet rays irradiated downward from an inside of the water cock for sterilization can be minimized from being emitted to the outside of the water cock.

Specifically, even if the user puts his/her fingers directly under the work cock in the course of irradiation of ultraviolet rays for sterilization of an inside of the water cock, there is an advantage that the user is not injured by ultraviolet rays.

In addition, there is an advantage that the sterilizing power of the water remaining in the water cock can reach the maximum sterilization effect of 99.9%.

In addition, there is an advantage that a structure for shielding the lower end of the water cock is not needed to prevent the external exposure of ultraviolet rays during the sterilization mode.

BEST MODE

Hereinafter, a water purifier including a water cock sterilization module according to an embodiment of the present invention will be described in detail with reference to the drawings.

Figure 1:
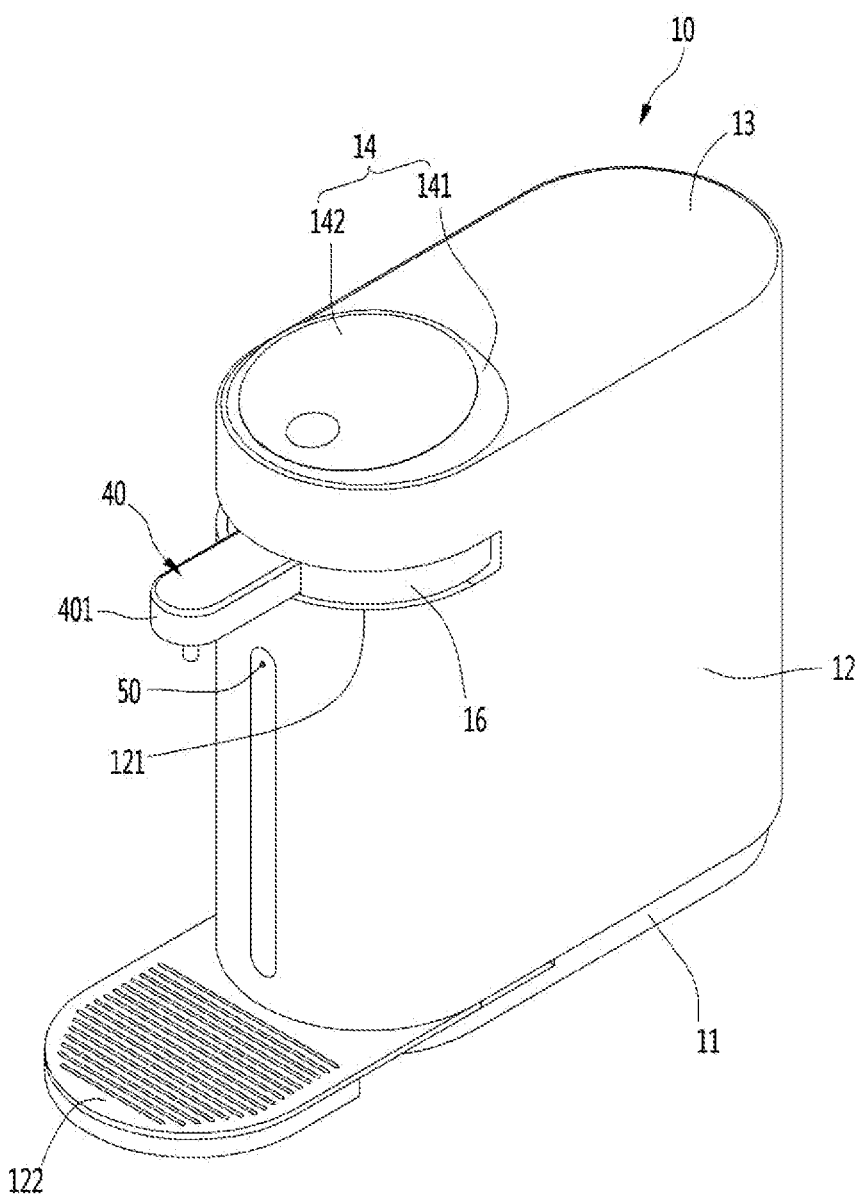
FIG. 1 is a perspective view illustrating a water purifier equipped with a water cock sterilization mechanism according to an embodiment of the present invention.

FIG. 1 is a perspective view illustrating a water purifier equipped with a water cock sterilization mechanism according to an embodiment of the present invention.

Referring to FIG. 1, the water purifier 10 according to the embodiment of the present invention may include a direct watering type cooling and heating water purifier for cooling or heating water directly supplied from an external water supply source and discharging the water, but is not limited thereto. In other words, the sterilization mechanism of the present invention can be also applied to a water purifier having a reservoir.

In detail, the water purifier 10 may include a base 11 constituting a bottom part, a housing 12 placed on an upper surface edge of the base 11, a cover 13 covering an opened upper surface of the housing 12, a control panel 14 formed on the upper surface of the cover 13, and a water chute 40 protruding from the outer circumferential surface of the housing 12.

More specifically, a part where the water chute 40 is formed may be defined as a front surface of the water purifier 10, and an opposite surface thereto may be defined as a rear surface of the water purifier 10.

In addition, the control panel 14 may be formed at a position close to the front end of the water purifier 10 and may be formed at a position close to the center part or the rear end of the water purifier 10 according to design conditions. In addition, the control panel 14 may be inclined in such a manner that the height of the control panel 14 increases toward the rear so that the control panel 14 can be easily recognized by the user's eyes positioned in front of the water chute 40.

In detail, the control panel 14 may include a panel main body 141 having a rear end protruding higher than the front end of the water purifier 10 from the upper surface thereof and a panel cover 142 covering the upper surface of the panel main body 141. In addition, the control panel 14 may include a plurality of operation buttons including a power button. For example, the operation buttons provided on the control panel 14 may include a power button, a water discharge button, a button for selecting the type of water to be discharged, a button for setting the water temperature, a button for setting the amount of water to be discharged, and the like.

In addition, the water chute 40 may be extended forward by a predetermined length from the front end of the water purifier 10 and may be rotatably mounted within a range of 90 degrees from the center of the front end of the water purifier 10 in a lateral direction, respectively. In other words, the water chute 40 can rotate 180 degrees in total. Of course, the water chute 40 may be fixed to the front surface of the housing 12.

In addition, a rotation guide 16 having a circular band shape may be mounted on the rear end of the water chute 40 so that the water chute 40 can rotate. The water chute 40 and the rotation guide 16 can be injection-molded into one body or can be formed as separate parts and joined as one body by a fastening member.

In addition, a guide hole 121 for guiding the rotation of the water chute 40 may be formed on the front surface of the housing 12 and the water chute 40 can rotate along the guide hole 121 by 90 degrees in the lateral direction. The water chute 40 may include a chute case 401.

In addition, a proximity sensor 50 for detecting the approach of the user is mounted on the front surface of the housing 12 so that in a case where the user approaches the water purifier 10 during sterilization, the proximity sensor can detect the approach of the user and thus can transmit the approach of the user to a control unit (not illustrated) of the water purifier. The control unit may be provided inside the control panel 14.

In addition, a tray 122 is mounted on the lower end of the front surface of the housing 12 so that a part of the water discharged from the water chute 40 or a water drop falling from the water chute 40 can be collected. The tray 122 may also be designed so as to be rotatable by a predetermined angle designed in the same manner as in the water chute 40 in the lateral direction.

Hereinafter, a sterilization mechanism according to an embodiment of the present invention provided in the water purifier will be described in detail with reference to the drawings.

Figure 2:
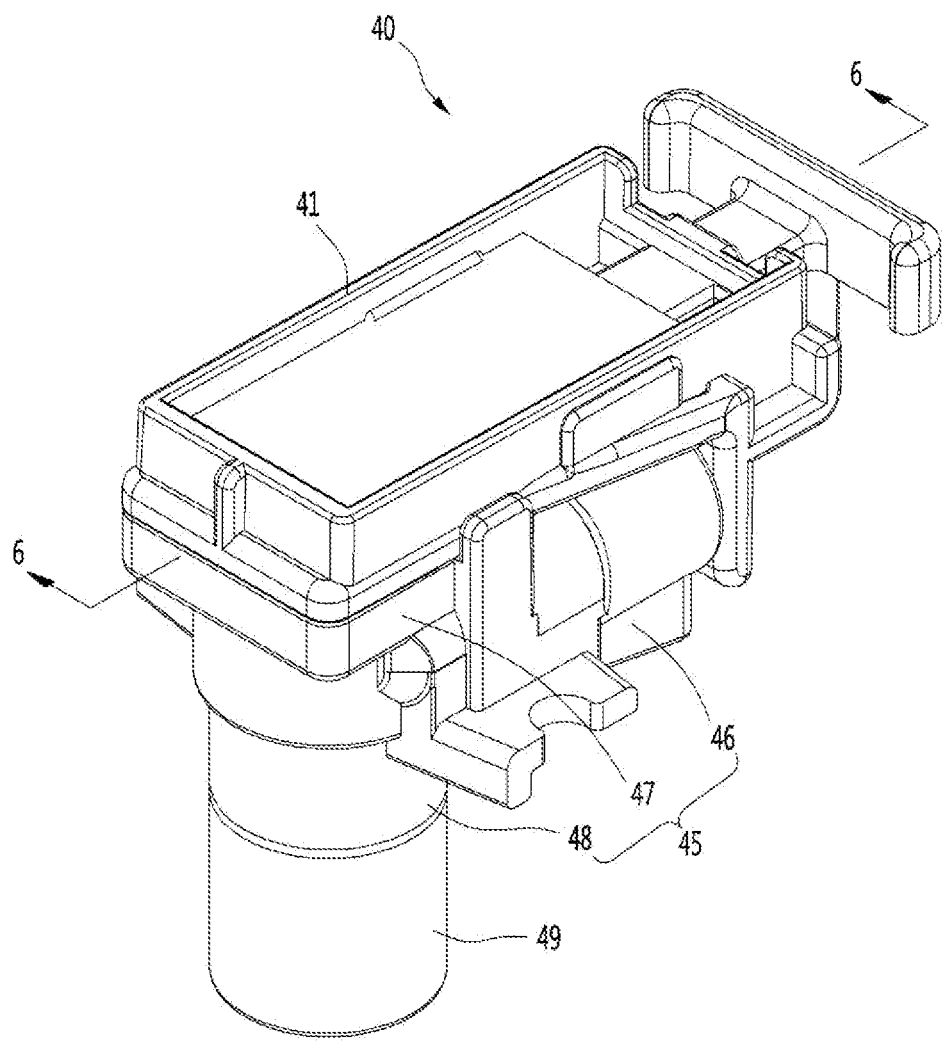
FIG. 2 is a perspective view illustrating a water chute in which a sterilization mechanism according to a first embodiment of the present invention is provided and a suitcase is removed.

FIG. 2 is a perspective view illustrating a water chute in which a sterilization mechanism according to a first embodiment of the present invention is provided and a suitcase is removed.

Referring to FIG. 2, the water chute 40 according to the first embodiment of the present invention may include the chute case 401, a water cock 45 accommodated in the chute case 401, a sterilization module 41 for sterilizing the interior of the water cock 45, and a safety guide 49 mounted on the water cock 45.

In detail, the water cock 45 may include a water inflow part 46 extending in the horizontal direction, a water outflow part 48 extending in the vertical direction at the end of the water inflow part 46, and a waterproof unit seating part 47 formed on an upper end of the water outflow part 48. The waterproof unit seating part 47 may be fixed to the bottom surface of the sterilization module 41 by being formed with the water outflow part 48 as one body.

Alternatively, the waterproof unit seating part 47 may be provided as an independent component, and the upper surface and the lower surface thereof may be fixed to the bottom surface of the sterilization module 41 and the upper surface of the water outflow part 48, respectively. In order to minimize leakage, the waterproof unit seating part 47 may be formed as a part of the water outflow part 48.

Hereinafter, the water chute in a state where the chute case 401 is removed is described based on the drawings, it is noted that the water chute 40 includes the chute case 401 even if there is no description above the chute case 401.

Figure 3:
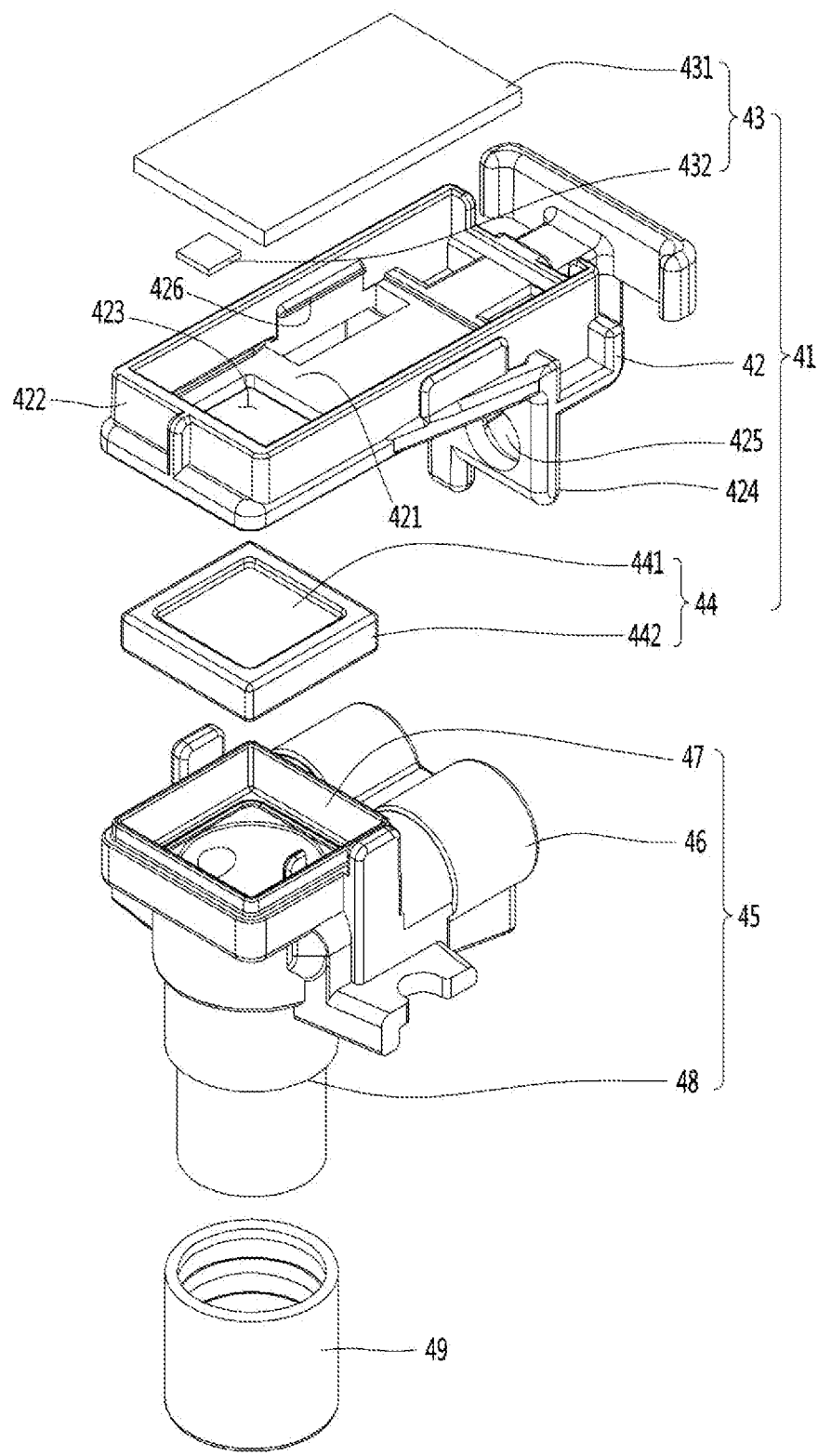
FIG. 3 is an exploded perspective view illustrating the water chute according to a first embodiment of the present invention.
Figure 4:
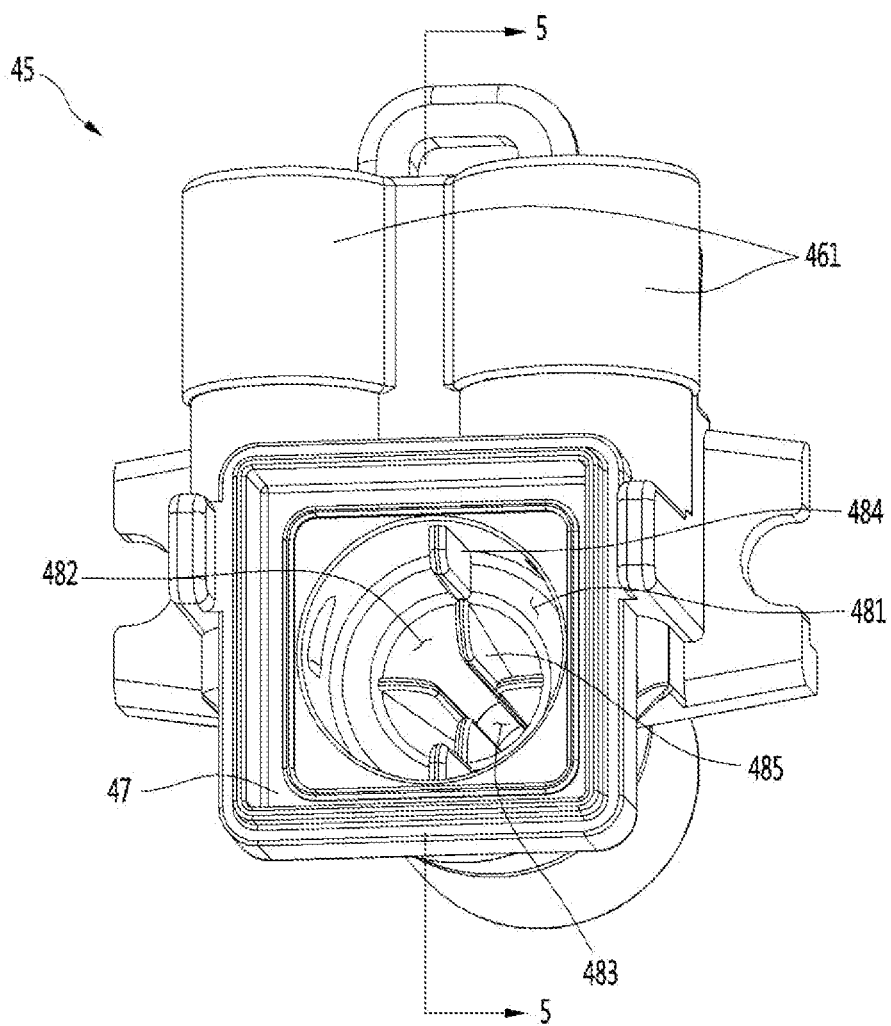
FIG. 4 is a perspective view illustrating a water cock constituting the water chute viewed from above.
Figure 5:
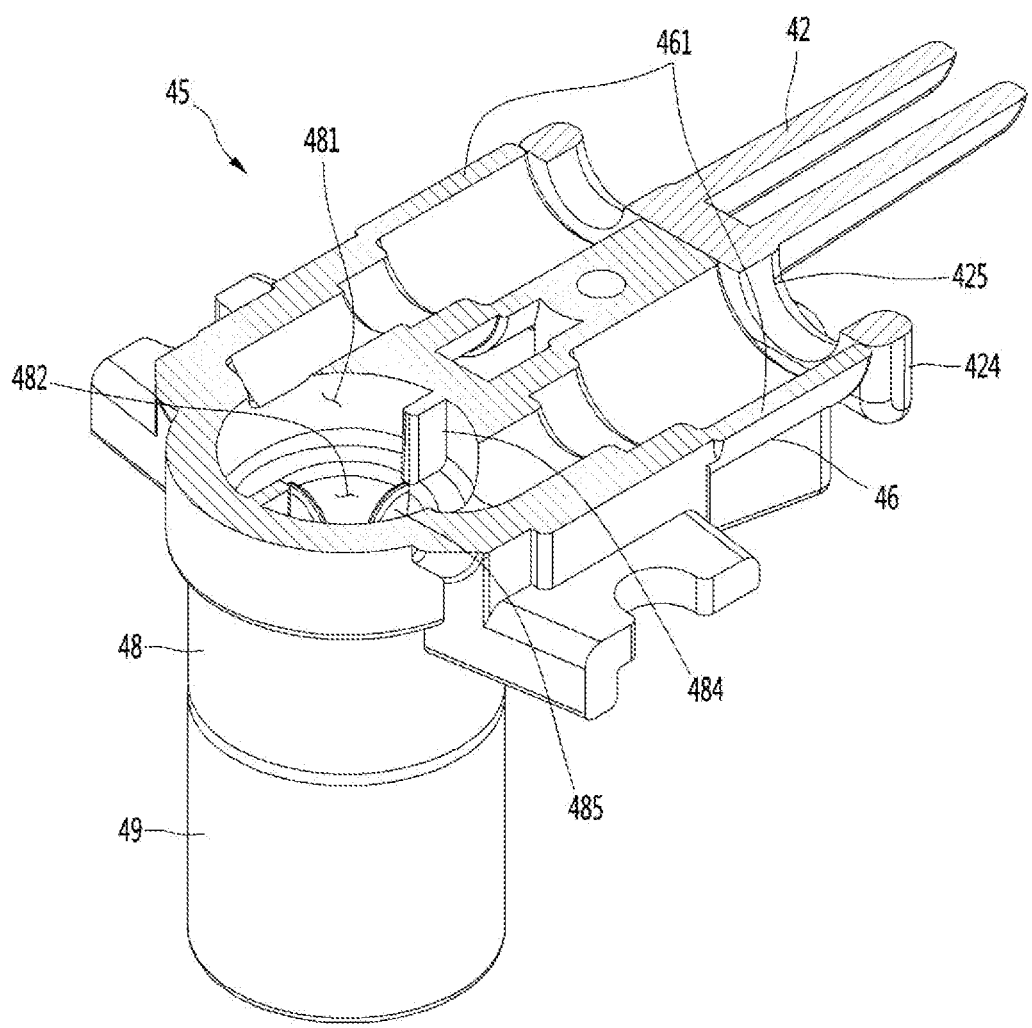
FIG. 5 is a cutaway perspective view of a water cock illustrating a cross-section cut along line 5-5 of FIG. 4.

FIG. 3 is an exploded perspective view illustrating the water chute according to a first embodiment of the present invention, FIG. 4 is a perspective view illustrating a water cock constituting the water chute viewed from above, and FIG. 5 is a cutaway perspective view of a water cock illustrating a cross-section cut along line 5-5 of FIG. 4.

Referring to FIGS. 3 to 5, the sterilization module 41 constituting the water chute 40 according to the first embodiment of the present invention may include a light emitting unit 43, a bracket 42 on which the light emitting unit 43 is mounted, and a waterproof unit 44 disposed below the bracket 42.

In detail, the light emitting unit 43 may include a light emitting element 432 which emits ultraviolet rays, and a substrate 431 on which the light emitting element 432 is mounted. In addition, the light emitting element 432 may be an LED element which emits ultraviolet rays having a wavelength of 300 nm to 400 nm, specifically, a wavelength of 380 nm.

In addition, the bracket 42 may include a bottom part 421, a wall part 422 which surrounds along the edge of the bottom part 421 and extending at a predetermined height, and a support rib 424 extending downward from a position spaced apart from a front end of the bottom part 421 to the rear side. In addition, a through-hole 423 (or a passage hole) through which the light emitted from the light emitting element 432 passes may be formed in the bottom part 421.

In addition, the wall part 422 may include a front wall and left and right side walls and a substrate support rib 426 may protrude from an inner surface of the left and right side walls to prevent the substrate 431 to be separated from the bracket 42.

In addition, one or a plurality of hose connection holes 425 may be formed in the support ribs 425.

In addition, the waterproof unit 44 is installed to prevent water flowing along the inside of the water cock 45 from splashing toward the light emitting element 432. Specifically, the waterproof unit 44 may include a transparent plate 441, and a sealer 442 surrounding the edge of the transparent plate 441. The transparent plate 441 may have a rectangular shape, as illustrated, or may have a polygonal or circular plate shape in addition thereto. The transparent plate 441 may be made of plastic or glass material.

Meanwhile, the water cock 45 may include a water inflow part 46, a water outflow part 48, and a waterproofing unit seating part 47 formed at the upper end of the water outflow part 48 as described above. As illustrated in FIG. 4, the waterproofing unit seating part 47 is formed with an accommodation space having a size to accommodate the waterproofing unit 44. Therefore, the accommodation space may have the same shape as the shape of the waterproof unit 44.

In addition, as illustrated in FIG. 5, the water inflow part 46 may include one or more water inflow ports 461. The water supply pipe connected to the water inflow port 461 may include a purified water pipe, a cold water pipe, a hot water pipe, an alkaline water pipe, and the like. The water inflow port 461 is provided as a number corresponding to the number of the connected water supply pipes or may be formed in a smaller number than the number of the connected water supply pipes.

For example, in a case where the cold water pipe and the purified water pipe share one water inflow port, as illustrated in the figure, the water inflow port 461 may include a cold water/purified water port and a hot water port.

Alternatively, it is also possible that the plurality of water supply pipes are designed to share a single water inflow port 461. In other words, an opening/closing valve may be installed at a part where the plurality of water supply pipes are gathered, and a pipe extending from an outlet end of the opening/closing valve may be connected to the single water inflow port.

Meanwhile, a water collecting part 481, a sloping part 482, and a straight part 483 may be formed in the water outflow part 48. The water collecting part 481, the sloping part 482, and the straight part 483 may be respectively defined as a first chamber, a second chamber, and a third chamber. The sloping part 482 and the straight part 483 may be defined as a water outflow passage. The water collecting part 481 may be defined as a part of the water inflow passage formed inside the water inflow part 46 or may be defined as a part of the water outflow passage.

In detail, the water collecting part 481 is a space in which the water flowing into the water inflow port 461 is gathered before falling to the water outflow part 48. In other words, the water collecting part 481 has a cylindrical shape having a predetermined diameter and depth (or length), and a discharge port of the water inflow port 461 may be formed on a side surface of the water collecting part 481.

The water discharged from the discharge port of the water inflow port 461 in the tangential direction of the water collecting part 481 can form a rotation current which rotates along the side surface of the water collecting part 481 due to inertia. The rotation current may act as a force which prevents water from flowing to the water outflow part 48.

In order to prevent such a rotation current, one or a plurality of partition ribs 484 may protrude from the side surface of the water collecting part 481 and the length of the partition rib 484 in the vertical direction may be the same as the length of the water collecting part 481 in the vertical direction. The width of the partition rib 484 may be shorter than the radius of the water collecting part 481.

In the present embodiment, two water inflow ports are connected to the water collecting part 481, and the outlets of the two water inflow ports are positioned opposite to each other so that a pair of partition ribs 484 are formed in the directions opposite to each other.

In addition, one or a plurality of partition ribs 485 may be formed on the inner circumferential surfaces of the sloping part 482 and the straight part 483. The partition rib 485 may extend continuously from the upper end of the sloping part 482 to the straight part 483 (see FIG. 6). The lower end of the partition rib 485 may extend to the lower end of the straight part 483 and may extend only to a position spaced upward from the lower end of the straight part 483.

As a further alternative, the partition ribs 485 formed in the sloping part 482 and the partition ribs formed in the straight part 483 can be spaced apart from each other in the circumferential direction of the water outflow part 48 and can be alternately disposed to each other. In this case, the partition ribs may function as a resistance structure to reduce the flow rate of water through the water outflow part 48.

Meanwhile, the cross sections of the water collecting part 481, the sloping part 482, and the straight part 483 may all be circular. The upper surface of the water collecting part 481 communicates with the bottom part of the waterproofing unit seating part 47 and the upper surface of the waterproofing unit seating part 47 can communicate with the through-hole 423 of the bracket 42.

Figure 6:
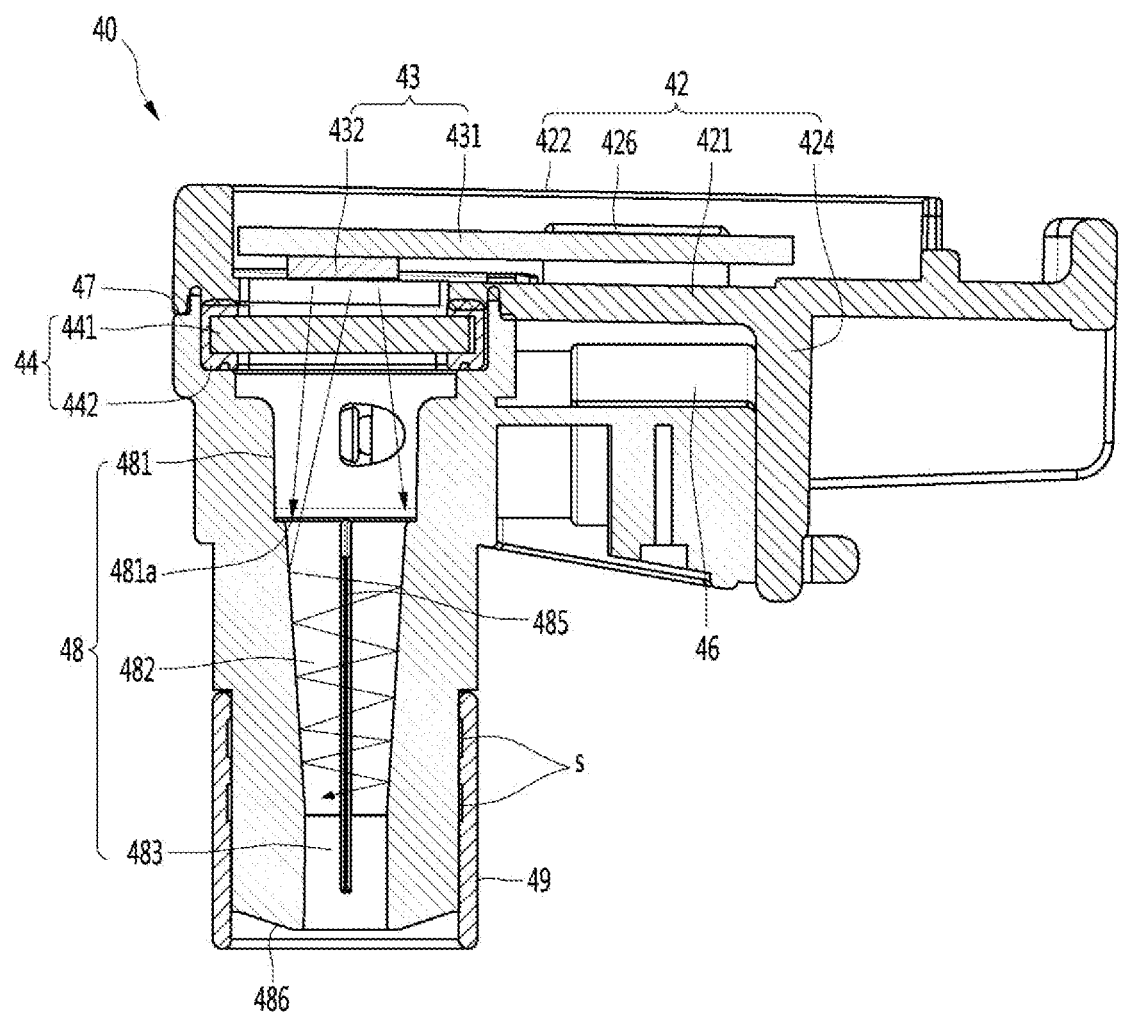
FIG. 6 is a longitudinal sectional view illustrating a water chute cut along line 6-6 in FIG. 2.

FIG. 6 is a longitudinal sectional view illustrating a water chute cut along line 6-6 in FIG. 2.

Referring to FIG. 6, a vertical line passing through the center of the light emitting element 432 coincides with a vertical line passing through the centers of the water collecting part 481, the sloping part 482, and the straight part 483.

In detail, the water collecting part 481 may be defined as a cylindrical chamber having a predetermined diameter and depth. The sloping part 482 may be defined as a chamber of a truncated cone in which the cross-sectional diameter gradually decreases toward the lower side.

The diameter of the upper end of the sloping part 482 may be smaller than the diameter of the water collecting part 481 so that a stepped part 481a may be formed between the water collecting part 481 and the sloping part 482.

The diameter of the upper end of the sloping part 482 and the sloping angle of the sloping part 482 may be determined in consideration of the amount and flow rate of water to be discharged.

In addition, the straight part 483 may be defined as a cylindrical chamber having a diameter equal to the diameter of the lower end of the sloping part 482 and extending to a predetermined length. The straight part 483 is formed at the lower end of the sloping part 482 so that the flow rate of the water to be discharged from the water outflow part 48 can be prevented from being excessively fast.

In addition, as illustrated in the figure, the lower end of the water outflow part 48 may be rounded convex downward toward the center part. Thus, the phenomenon of water being formed at the lower end of the straight part 483 can be minimized.

In addition, the lower end of the safety guide 49 may extend slightly beyond the lower end of the water outflow part 48 so that the lower end of the water outflow part 48 is not exposed to the user. One or a plurality of friction rings s are provided on the inner circumferential surface of the safety guide 49 to prevent the safety guide 49 from being separated from the outer circumferential surface of the water outflow part 48.

Alternatively, the safety guide 49 may be coupled to the outer circumferential surface of the water outflow part 48 in a screw thread coupling manner.

As a further alternative, it is also possible that the cylindrical guide rib is further extended from the lower end edge of the water outflow part 48, without the safety guide 49. In other words, the lower end of the extending rib may extend further down than the lower end of the straight part 483, so that the lower end of the straight part 483 is not exposed to the outside.

Meanwhile, as illustrated in FIG. 6 by the arrow, a part of the ultraviolet ray emitted from the light emitting element 432 is reflected toward the side surface of the collecting part 481 by colliding with the stepped part 481*a*.

The ultraviolet rays colliding with the inner circumferential surface of the sloping part 482 disappear before reaching the straight part 483 through a plurality of reflection processes.

The ultraviolet rays irradiated vertically from the center of the light emitting element 432 may be emitted to the outside through the straight part 483. However, the amount of emitted ultraviolet rays is insignificant enough not to damage the user's skin.

According to this structure, there is an advantage that ultraviolet rays emitted from the light emitting element 432 maximize the residual water sterilization efficiency remaining in the inner circumferential surface of the water outflow part 48 and the water outflow part 48, while the amount of ultraviolet rays emitted to the outside of the water outflow part 48 can be minimized.

Figure 7:
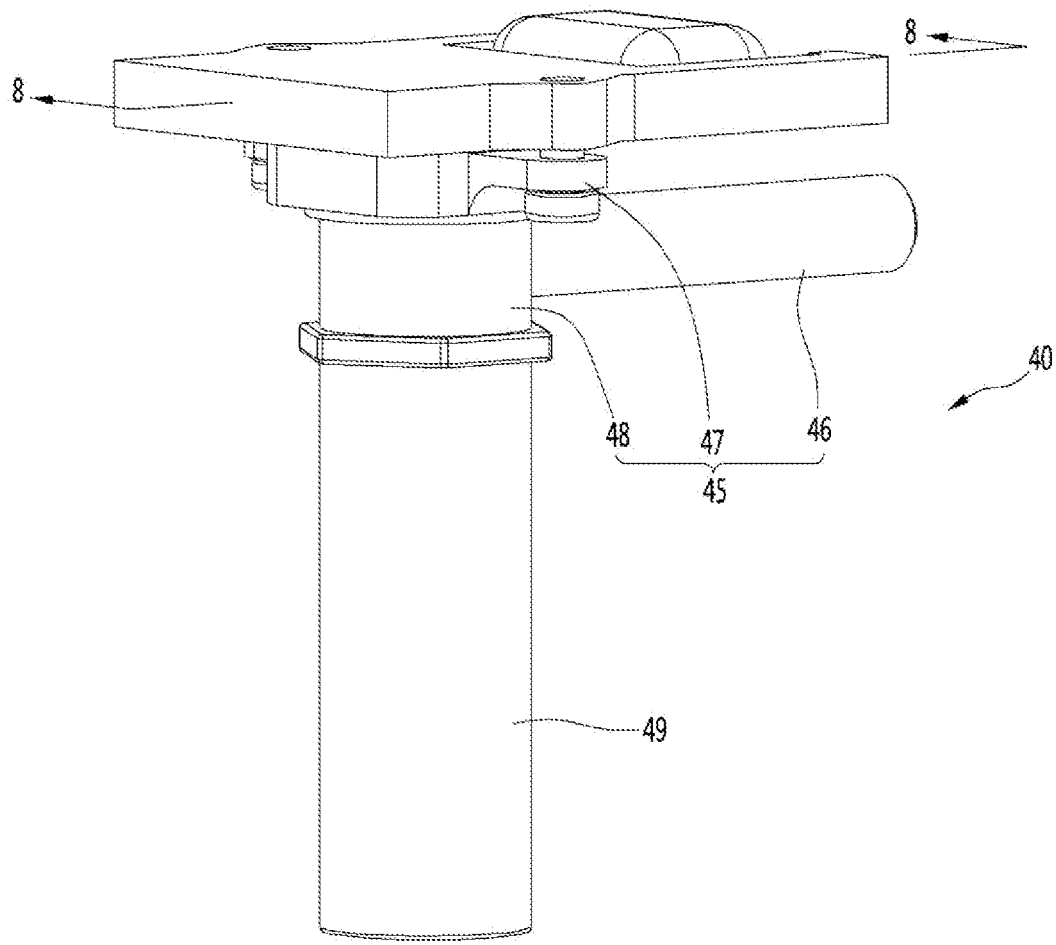
FIG. 7 is a perspective view illustrating a water chute according to a second embodiment of the present invention.
Figure 8:
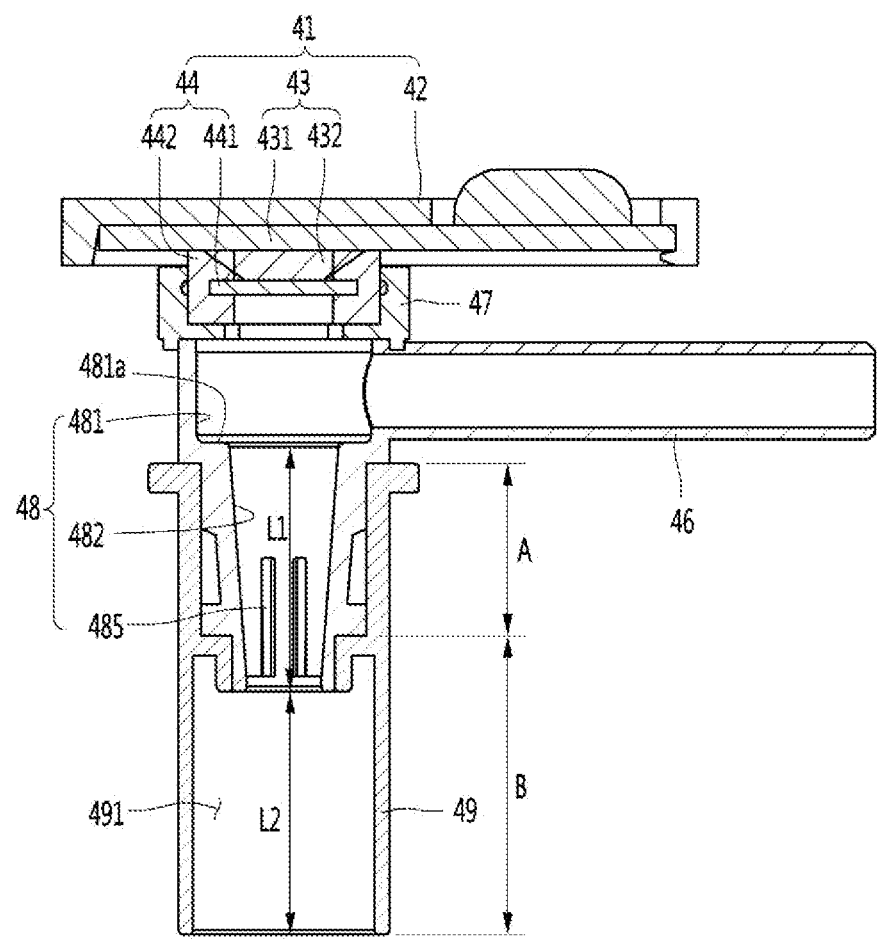
FIG. 8 is a longitudinal sectional view taken along line 8-8 in FIG. 7.

FIG. 7 is a perspective view illustrating a water chute according to a second embodiment of the present invention, and FIG. 8 is a longitudinal sectional view taken along line 8-8 in FIG. 7.

Referring to FIGS. 7 and 8, a water chute 40 according to a second embodiment of a present invention may include a sterilization module 41, and a water cock 45 which is disposed below the sterilization module 41, and the water cock 45 may include the water inflow part 46, a waterproofing unit seating part 47, and a water outflow part 48.

In addition, the sterilization module 41 may include a bracket 42, a light emitting unit 43 mounted on the bracket 42, and a waterproofing unit 44 seated on the waterproofing unit seating part 47.

In addition, the water outflow part 48 includes the water collecting part 481 and the sloping part 482, the diameter of the upper end of the sloping part 482 may be formed to be smaller than the diameter of the water collecting part 481, and thus a stepped part 481*a* may be formed between the water collecting part 481 and the sloping part 482.

The characteristics of the sterilizing mechanism according to the second embodiment of the present invention differing from the sterilizing mechanism according to the first embodiment is that the lower end of the safety guide 491 further extends a predetermined length from the lower end of the water outflow part 48, and thus a shielding space 491 for blocking exposure of ultraviolet rays is formed inside the safety guide 491.

In detail, the cross-sectional diameter of the shielded space 491 is formed to be larger than the diameter of the lower end of the water outflow part 48, so that the potable water discharged from the water outflow part 48 is prevented from being splashed to the inner surface of the safety guide 49 a much as possible.

In addition, a part of the ultraviolet ray passing through the center of the water outflow part 48 can be extinguished before passing through the lower end of the shielding space 491.

Specifically, the distance L1 (which may be defined as an 'ultraviolet ray extinction section') from the lower end of the water collecting part 481 (or the upper end of the sloping part 482) to the lower end of the water outflow part 48 may be the same as or longer than the distance L2 (which may be defined as the 'length of the shielded space') from the lower end of the water outflow part 48 to the lower end of the safety guide 49.

The safety guide 49 may be divided into a coupling section A to be coupled to the water outflow part 48 and an ultraviolet shielding section B to form the shielding space 491.

Figure 9:
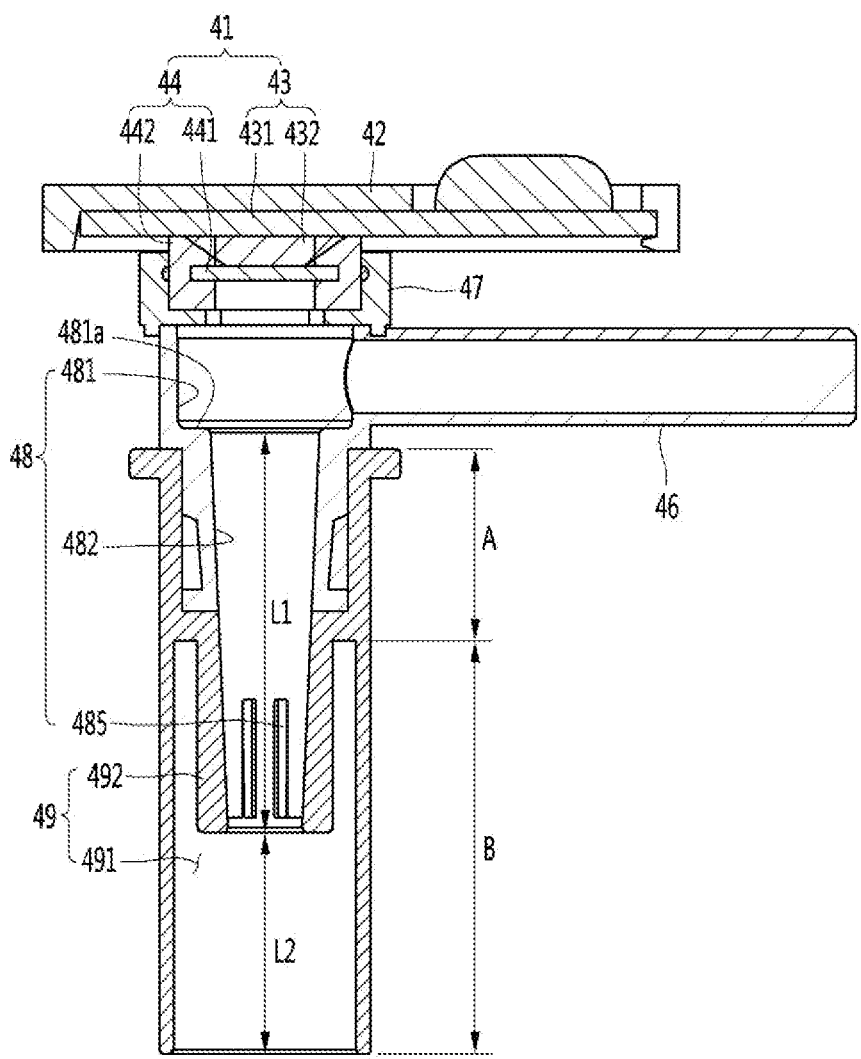
FIG. 9 is a longitudinal sectional view illustrating an internal structure of a water chute according to a third embodiment of the present invention.

FIG. 9 is a longitudinal sectional view illustrating an internal structure of a water chute according to a third embodiment of the present invention.

Referring to FIG. 9, the water chute 40 according to the third embodiment of the present invention is different from the water chute 40 according to the second embodiment of the present invention in a feature in which the ultraviolet ray extinction structure is further extended into the shielding space 491 formed in the safety guide 49 and the other configurations thereof in addition to the above configurations are the same as those of the second embodiment. In addition, the same reference numerals as those of the second embodiment will not be repeatedly described.

In detail, a shielding space 491 is formed in the safety guide 49 and an extended part 492 is formed in the shielding space. In the extended part 492, an extension passage continuously connected to an outflow passage formed inside the water outflow part 482 is formed.

In detail, the extension passage may include a truncated cone-shaped sloping part which gradually decreases in cross-sectional diameter toward the lower end as illustrated in the figure.

The diameter of the upper end of the sloping part formed inside the extended part 492 may be the same as the diameter of the lower end of the sloping part 482 formed in the water outflow part 48. In other words, a sloping part whose cross-sectional diameter gradually decreases from the lower end of the water collecting part 481 to the lower end of the extended part 492 is formed so that a part of the light emitted from the light emitting element 432 is extinguished while being reflected on the inner circumferential surface of the sloping part.

Further, since the sloping part structure extends to the inside of the shielding space 491, the possibility of external emission of ultraviolet rays can be further reduced. The sloping part is further extended into the shielding space 491 so as to minimize the external emission of ultraviolet rays so that the length L1 of the ultraviolet rays extinction section, that is, the length reaching the lower end of the extended part 492 from the lower end of the water collecting part 481 may be longer than the length L2 of the shielding space 491.

Here, the extended part 492 may be a part of the safety guide 49 or a part of the water outflow part 48.

In addition, the sloping part 482 formed inside the water outflow part 48 may be defined as a first sloping part and the sloping part formed inside the extended part 492 may be defined as a second sloping part. The inclination of the first sloping part may be the same as the inclination of the second sloping part or may be smaller than the inclination of the second sloping part.

Here, the inclination may be defined as a magnitude of an angle formed by a straight line passing through the upper end of the sloping part and a straight line passing through the inner peripheral surface of the sloping part.

Therefore, the fact that the inclination of the first sloping part is smaller than the inclination of the second sloping part means that the degree of decrease of the cross-sectional diameter toward the lower end is small.

However, it is also possible that the inclination of the second sloping part is formed to be smaller than the inclination of the first sloping part, considering the flow rate of water discharged from the water outflow part 48.

In addition, the extension passage may include a straight part of a cylindrical shape as illustrated in the first embodiment. In other words, it is also possible that a cylindrical extension passage having a constant cross-sectional diameter is formed in the extended part 492. This can mean that the inclination of the second sloping part is 0 degree.

In summary, the inclination of the second sloping part can be appropriately selected in consideration of the flow rate and resistance of the water to be discharged and the degree of exposure of ultraviolet rays to the outside.

In addition, one or a plurality of partition ribs 485 may be formed on the inner circumferential surface of the second sloping part, that is, the inner circumferential surface of the extension passage. The partition ribs 485 formed on the inner circumferential surface of the second sloping part may be formed to coincide with the partition ribs formed on the inner circumferential surface of the first sloping part, and the partition rib may be formed at a position shifted by a predetermined angle in the circumferential direction of the water outflow part 48.

The invention claimed is:

1. A liquid dispenser comprising:
a housing, the housing accommodating at least one component to generate at least one of a cooled liquid or a heated liquid; and
a liquid chute that protrudes from a front surface of the housing,
wherein the liquid chute includes
a liquid cock through which the at least one of the cooled liquid or the heated liquid flows; and
a light emitting element that is mounted on the liquid cock to emit ultraviolet rays, and
wherein the liquid cock includes:
a liquid inflow part that extends in a transverse direction and includes a liquid inflow passage formed therein;
a liquid outflow part that extends in a direction intersecting the liquid inflow part at an end of the liquid inflow part and includes a liquid outflow passage formed therein; and
a plurality of first partition ribs protruding from an inner surface of the liquid outflow part to be located in the liquid outflow passage, wherein the plurality of first partition ribs extend vertically and are spaced apart from each other in a circumferential direction of the liquid outflow passage.

2. The liquid dispenser of claim 1, wherein the light emitting element is positioned on an upper end of the liquid outflow part, and at a position that is upwardly spaced apart from upper ends of the plurality of first partition ribs.

3. The liquid dispenser of claim 2, wherein the liquid outflow passage includes:
a sloping part having a truncated cone shape in which a cross-sectional diameter thereof gradually decreases toward a lower end thereof.

4. The liquid dispenser of claim 3, wherein the sloping part extends to a lower end of the liquid outflow part.

5. The liquid dispenser of claim 3, further comprising at least one of:
a cylindrical liquid collecting part that is formed inside the liquid cock and corresponding to an area where the liquid inflow part and the liquid outflow part intersect; or a straight part that extends from the lower end of the sloping part to a lower end of the liquid outflow part, the straight part having a constant cross-sectional diameter,
wherein the sloping part extends from a lower end of the cylindrical liquid collecting part.

6. The liquid dispenser of claim 5, wherein the plurality of partition ribs are formed in the sloping part and the straight part.

7. The liquid dispenser of claim 5, wherein a diameter of an upper end of the sloping part is formed to be smaller than a diameter of a bottom part of the liquid collecting part, such that a stepped part is formed on the bottom part of the liquid collecting part.

8. The liquid dispenser of claim 1, wherein a lower end of the liquid outflow part is convexly rounded.

9. The liquid dispenser of claim 5, further comprising:
a bracket that is coupled to the liquid cock, the bracket being configured to support the light emitting element, and
a liquid-proof unit that is positioned between the liquid collecting part and the light emitting element, the liquid-proof unit being configured to prevent liquid collected in the liquid collecting part from splashing to the light emitting element,
wherein a seating part that seats the liquid-proof unit is formed inside the liquid outflow part and corresponds to an upper end of the liquid collecting part.

10. The liquid dispenser of claim 9, wherein the liquid-proof unit includes:
a transparent plate that includes a transparent material, and
a sealer that surrounds an edge of the transparent plate.

11. The liquid dispenser of claim 1, further comprising:
a safety guide that is coupled to an outer circumferential surface of the liquid outflow part,
wherein the safety guide is fixedly or detachably coupled to the liquid outflow part.

12. The liquid dispenser of claim 11, wherein the safety guide includes:
a coupling section that is coupled to the outer circumferential surface of the liquid outflow part, and
a shielding section that is provided below the coupling section and in which a shielding space is formed.

13. The liquid dispenser of claim 12, further comprising:
an extension part that is formed within the shielded space,
wherein the liquid outflow passage includes a sloping part having a truncated cone shape in which a cross-sectional diameter thereof gradually decreases toward a lower end thereof, and
wherein the extension part includes an extension passage that is continuously connected to the sloping part of the liquid outflow passage.

14. The liquid dispenser of claim 13, wherein the extension passage includes one of:
a sloping section having a diameter at an upper end thereof that corresponds to a diameter of the lower end of the sloping part of the liquid outflow passage, and that has a reduced cross-sectional diameter toward a lower end of the sloping section; and
a straight part that has a constant cross-sectional diameter.

15. The liquid dispenser of claim 13, further comprising:
a plurality of second partition ribs that are formed in the extension passage,
wherein the plurality of second partition ribs are integrally formed with the plurality of first partition ribs or are positioned so as to be spaced apart and separated from the first partition ribs in a circumferential direction of the extension passage.

16. The liquid dispenser of claim 13, wherein the extension part is a part of the liquid outflow part.

17. The liquid dispenser of claim 13, wherein the extension part is a part of the safety guide.

18. The liquid dispenser of claim 1, further comprising:
a proximity sensor that is mounted on a front surface of the housing.

* * * * *